United States Patent
Cupp et al.

(10) Patent No.: US 6,825,168 B2
(45) Date of Patent: Nov. 30, 2004

(54) ANTITHROMBIN PROTEIN AND DNA SEQUENCES FROM BLACK FLY

(75) Inventors: Mary S. Cupp, Auburn, AL (US); Eddie W. Cupp, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 10/196,117

(22) Filed: Jul. 16, 2002

(65) Prior Publication Data

US 2003/0165493 A1 Sep. 4, 2003

Related U.S. Application Data

(60) Continuation of application No. 09/556,166, filed on Apr. 21, 2000, now Pat. No. 6,465,214, which is a division of application No. 09/036,113, filed on Mar. 6, 1998, now Pat. No. 6,077,825.
(60) Provisional application No. 60/040,683, filed on Mar. 13, 1997.

(51) Int. Cl.$^7$ .................. A61K 38/16; C07K 14/00; C12N 15/15; C12N 5/10
(52) U.S. Cl. .................. 514/12; 514/2; 435/69.1; 435/325; 435/348; 435/252.3; 435/254.11; 536/23.5; 536/23.1; 530/300; 530/381
(58) Field of Search .................. 435/348, 325, 435/252.3, 254.11, 69.1; 530/300, 381; 536/23.5, 23.1; 514/2, 12

(56) References Cited

U.S. PATENT DOCUMENTS

| | | | |
|---|---|---|---|
| 5,196,403 A | 3/1993 | Maraganore et al. |
| 5,356,875 A | 10/1994 | Sarmientos et al. |
| 5,439,820 A | 8/1995 | Sarmientos et al. |
| 5,472,942 A | 12/1995 | Sawyer et al. |

OTHER PUBLICATIONS

Webster's II New Riverside University Dictionary, A. H. Soukhanov, Sr. Ed.(The Riverside Publishing Company: USA), p. 68, 1994.*

Abebe et al., "Anticoagulant Activity In Salivary Gland Extracts of Black Flies (Diptera: Stimuliidae)," *J. Med. Entomol*, 1994, pp. 908–911, vol. 31, No. 6.

Abebe et al., "Simulidin: A Black Fly (*Simulium vittatum*) Salivary Gland Protein With Anti-thrombin Activity," *J. Inset Physiol.*, 1995, pp. 1001–1006, vol. 41, No. 11.

Abebe et al. , "Novel Anticoagulant From Salivary Glands of *Simulium vittatum* (Diptera: Simuliidae) Inhibits Activity of Coagulation Factor V," *J. Med. Entomol.*, 1996, pp. 173–176, vol. 33, No. 1.

Blankenship et al., "Amino Acid Sequence of Ghilaten: Anticoagulant–Antimetastatic Principle of the South American Leech, *Haementeria Ghilianii*," *Biochem, Biophys. Res. Comm.*, Feb. 14, 1990, pp. 1384–1389, vol. 166, No. 3.

Han et al., "Cloning and Expression of cDNA Encoding Antistasin, a Leech–derived Protein Having Anti–coagulant and Anti–metastatic Properties," *Gene*, Jan. 1989, pp. 47–57, vol. 75, No. 1.

Harvey et al., "Cloning and Expression of a cDNA Coding for the Anticoagulant Hirudin from the Bloodsucking Leech, *Hirudo medicinalis*," *Proc. Natl. Acad. Sci.* USA, Feb. 1986, pp. 1084–1088, vol.83, No. 4.

Jacobs et al., "Isolation and Characterization of a Coagulation Factor Xa Inhibitor from Black Fly Salivary Glands," *Thrombosis and Haemostasis*, 1990, pp. 235–238, vol. 64, No. 235.

Sun et al., "Purification, Characterization and cDNA Cloning of a Novel Anticoagulant of the Intrinsic Pathway, (Prolixin–S), from Salivary Glands of the Blood Sucking Bug, *Rhodnius prolixus*," *Thrombosis and Haemostasis*, Apr. 1996, pp. 573–577, vol. 75, No. 4.

* cited by examiner

Primary Examiner—Lorraine Spector
Assistant Examiner—Claire M. Kaufman
(74) Attorney, Agent, or Firm—Alston & Bird LLP

(57) ABSTRACT

The invention is drawn to anti-thrombin proteins from the salivary glands of the species, *Simulium*. Methods for recombinant production of the protein as well as biomedical uses are provided.

4 Claims, No Drawings though it is recognized that proteins containing greater than 75% homology, such as proteins of 80% homology or greater, are considered to fall within the scope of this invention as well.

ANTITHROMBIN PROTEIN AND DNA SEQUENCES FROM BLACK FLY

CROSS-REFERENCE TO RELATED APPLICATIONS

This application is a continuation of U.S. application Ser. No. 09/556,166, filed Apr. 21, 2000, now U.S. Pat. No. 6,465,214 issued Oct. 15, 2002, which is a divisional of U.S. application Ser. No. 09/036,113, filed Mar. 6, 1998, now U.S. Pat. No. 6,077,825, issued Jun. 20, 2000, which claims the benefit of U.S. Provisional Application No. 60/040,683, filed Mar. 13, 1997, each of which is hereby incorporated in its entirety by reference herein.

FIELD OF THE INVENTION

The present invention relates to medical treatments utilizing antithrombin proteins.

BACKGROUND OF THE INVENTION

Thromboembolic diseases are among the most important circulatory diseases. A thrombin is a blood clot that partially or completely blocks blood flow through a blood vessel. An embolus is a thrombus that has formed elsewhere in the body, broken free, and traveled to the site where blockage occurs. Blockage in the brain results in a stroke, i.e., a cerebral infarction, a localized area of dead cells. An embolus in a lung can produce pulmonary embolism, one of the principal lung diseases in bed-ridden patients. Bed ridden and elderly persons are also particularly prone to thrombophlebitis, which is a blockage of circulation in a leg caused by an embolus. An embolus or thrombus lodging in one of the blood vessels serving the heart causes necrosis of part of the heart tissue, a myocardial infarction, commonly called a heart attack.

The initiating event of many myocardial infarctions is the hemorrhage into atherosclerotic plaques. Such hemorrhage often results in the formation of a thrombus (or blood clot) in the coronary artery which supplies the infarct zone. This thrombus is composed of a combination of fibrin and blood platelets. The formation of a fibrin-platelet clot has serious clinical ramifications. The degree and duration of the occlusion caused by the fibrin-platelet clot determines the mass of the infarct zone and the extent of damage.

The formation of fibrin-platelet clots in other parts of the circulatory system may be partially prevented through the use of anticoagulants, such as heparin. Unfortunately, heparin has not been found to be universally effective in preventing re-occlusion in myocardial infarction victims in which the degree of blood vessel occlusion is greater than or equal to 70%, particularly in those patients with severe residual coronary stenosis. Among the more promising of the agents are hirudin and its analogs, which bind to and inactivate thrombin. Hirudin has a theoretical advantage over heparin as an anti-thrombotic agent. Thrombin bound to thrombi or platelets is relatively protected from inhibition by heparin while hirudin, at least in vitro, is still effective. Other promising investigational agents include fibrinogen receptor antagonists, which block platelet aggregation and dense granule release by a mechanism distinct from that of aspirin, and inhibitors of thromboxane production.

There is therefore a need for additional antithrombin agents which exhibit low toxicity, little or no antigenicity, and a very short clearance time from circulation.

SUMMARY OF THE INVENTION

Antithrombin proteins and DNA sequencing coding the proteins are provided. The protein named simulidin is isolated from *Simulium* Spp. The proteins are useful in medical treatments where antithrombin agents are needed.

Methods for preparation and administration of the proteins are additionally provided.

DETAILED DESCRIPTION OF THE INVENTION

Methods and compositions for use as antithrombin agents are provided. The agents have an inhibitory effect on thrombin. The proteins are from black flies (Simuliidae) and other hematophagous Diptera belonging to the sub order Nematocera, particularly from *Simulium ssp*. The protein has been designated simulidin. A major function of the proteins of the invention is 1) to delay hemostasis by the abrogation of clotting by eliminating the formation of a fibrin network through initiation of the α-form of thrombin, and 2) inhibition of platelet aggregation stimulated by thrombin.

The compositions of the invention comprise antithrombin proteins from the salivary gland of the blood-feeding black fly. The proteins exhibit antithrombin activity as well as the ability to interfere with macrophage function. Substantially purified preparations of the protein are provided. Such substantially purified preparations include proteins substantially free of any compound normally associated with the protein in its natural state. Such proteins can be assessed for purity by SDS-PAGE, chromatography, electrophoresis or other methods. See, M. P. Deutscher (ed.), *Guide to Protein Purification*, Academic Press, Inc. (1990).

The terms "substantially pure" or "substantially purified" are not meant to exclude artificial or synthetic mixtures of the protein with other compounds. It is recognized that the antithrombin proteins of the present invention include those proteins homologous to, and having essentially the same biological properties as, the antithrombin protein described herein, and particularly the protein disclosed herein in SEQ ID NO:2. This definition is intended to encompass natural allelic variations in the genes.

The invention additionally encompasses the nucleotide sequences which encode the proteins of the invention. The nucleotide sequence of the coding sequence from *S. vittatum* is provided in SEQ ID NO:1. Additionally, cloned genes of the present invention can be of other species of origin. Such species include, but are not limited to *S. argus, S. ochraceum*, and *S. metallicum*.

DNAs which hybridize to the nucleotide sequence of the antithrombin gene from the black fly are also an aspect of this invention. Conditions, which will permit other DNAs to hybridize to the DNA disclosed herein, can be determined in accordance with known techniques. For example, hybridization of such sequences may be carried out under conditions of reduced stringency, medium stringency or even stringent conditions (e.g., conditions represented by a wash stringency of 35–40% Formamide with 5×Denhardt's solution, 0.5% SDS and 1×SSPE at 37° C.; conditions represented by a wash stringency of 40–45% Formamide with 5×Denhardt's solution, 0.5% SDS, and 1×SSPE at 42° C.; and conditions represented by a wash stringency of 50% Formamide with 5×Denhardt's solution, 0.5% SS and 1×SSPE at 42° C., respectively, to DNA encoding the genes disclosed herein in a standard hybridization assay. See J. Sambrook et al., Molecular Cloning, A Laboratory Manual (2d Ed. 1989) (Cold Spring Harbor Laboratory)).

In general, sequences which code for the antithrombin protein and hybridize to the nucleotide sequence disclosed herein will be at least 75% homologous, 85% homologous, and even 95% homologous or more with the sequences. Further, the amino acid sequences of the antithrombin proteins isolated by hybridization to the DNA's disclosed herein are also an aspect of this invention. The degeneracy of the genetic code, which allows different nucleic acid sequences to code for the same protein or peptide, is well known in the literature. See, e.g., U.S. Pat. No. 4,757,006.

The hybridization probes may be cDNA fragments or oligonucleotides, and may be labeled with a detectable group as known in the art. Pairs of probes which will serve as PCR primers for the antithrombin gene or a protein thereof may be used in accordance with the process described in U.S. Pat. Nos. 4,683,202 and 4,683,195.

The polypeptides of the invention may be subject to one or more post-translational modifications such as sulphation, COOH-amidation, acylation or chemical of the polypeptide chain.

It is recognized that the nucleotide and peptide sequences of the invention may be altered in various ways including amino acid substitutions, deletions, truncations, and insertions. Methods for such manipulations are generally known in the art. For example, amino acid sequence variants of the peptides and proteins can be prepared by mutations in the DNA. Methods for mutagenesis and nucleotide sequence alterations are well known in the art. See, for example, Kunkel, T. (1985) *Proc. Natl. Acad. Sci. USA* 82:488–492; Kunkel et al. (1987) *Methods in Enzymol.* 154:367–382; U.S. Pat. No. 4,873,192; Walker and Gaastra (eds.) *Techniques in Molecular Biology*, MacMillan Publishing Company, NY (1983) and the references cited therein. Thus, the nucleotide sequences of the invention include both the naturally occurring sequences as well as mutant forms. Likewise, the peptides and proteins of the invention encompass both naturally occurring and modified forms thereof. Such variants will continue to possess the desired activity. Obviously, the mutations that will be made in the DNA encoding the variant must not place the sequence out of reading frame and preferably will not create sequences deleterious to expression of the gene product. See, EP Patent Application Publication No. 75,444.

Thus proteins of the invention include the naturally occurring forms as well as variants thereof. These variants will be substantially homologous and functionally equivalent to the native protein. A variant of a native protein is "substantially homologous" to the native protein when at least about 80%, more preferably at least about 90%, and most preferably at least about 95% of its amino acid sequence is identical to the amino acid sequence of the native protein. A variant may differ by as few as 1, 2, 3, or 4 amino acids. By "functionally equivalent" is intended that the sequence of the variant defines a chain that produces a protein having substantially the same biological activity as the native protein of interest. Such functionally equivalent variants that comprise substantial sequence variations are also encompassed by the invention. Thus a functionally equivalent variant of the native protein will have a sufficient biological activity to be therapeutically useful. By "therapeutically useful" is intended effective in achieving a therapeutic goal as discussed below.

Methods are available in the art for determining functional equivalence. Biological activity can be measured using assays specifically designed for measuring activity of the native protein, including assays described in the present invention. Additionally, antibodies raised against the biologically active native protein can be tested for their ability to bind to the functionally equivalent variant, where effective binding is indicative of a protein having conformation similar to that of the native protein. DNA sequences can also be synthesized chemically or modified by site-directed mutagenesis to reflect the codon preference of the host cell and increase the expression efficiency.

The proteins of the invention can be "engineered" in accordance with the present invention by chemical methods or molecular biology techniques. Molecular biology methods are most convenient since proteins can be engineered by manipulating the DNA sequences encoding them. Genomic DNA, cDNA, synthetic DNA, and any combination thereof may be used for this purpose. Genomic DNA sequences or cDNA sequences encoding proteins can be isolated based on the amino acid sequence of proteins or certain protein properties. Many methods of sequence isolation are known in the art of molecular biology. See particularly Sambrook et al. (1989) *Molecular Cloning: A Laboratory Manual* (Cold Spring Harbor Laboratory Press, Plainview, N.Y.), herein incorporated by reference.

To produce an antithrombin polypeptide by recombinant DNA technology, a gene encoding a polypeptide of the invention is prepared. The DNA coding sequence typically does not contain introns. The DNA sequence is isolated and purified, the gene is inserted in an expression vector able to drive expression and production of the recombinant product. The DNA sequence may be a cDNA sequence. The DNA sequence may be a synthetic DNA sequence. The synthetic gene is typically prepared by chemically synthesizing oligonucleotides which, in total, correspond to the desired gene. The synthesized oligonucleotides are then assembled to obtain the gene.

If desired, the gene sequence may be modified by site-directed mutagenesis to introduce one or more coding changes. Typically, a gene is constructed with restriction sites at each end to facilitate its subsequent manipulation.

A DNA sequence may be provided which further encodes a leader peptide. The leader peptide is capable of directing secretion of the polypeptide from cells in which the polypeptide is to be expressed. The sequence encoding the leader peptide is typically fused to the 5'-end of the DNA sequence encoding the polypeptide. Leader sequences are known in the art and include the OmpA leader peptide, the leader peptide of vesicular stomatitis virus G protein (VSV G protein). The OmpA leader is useful when expression is in a bacterial host, such as *E. coli* while the VSVG protein is useful when expression is in insect cells.

The DNA sequence may be provided with a cleavable site to release the polypeptide of the invention. A DNA sequence may be used which encodes a carrier polypeptide sequence fused via a cleavable linkage to the end-terminus of a polypeptide of the invention. The cleavable linkage may be one cleavable by cyanogen bromide. For expression of the polypeptides, an expression vector is constructed which comprises a DNA sequence encoding the polypeptide which is capable of expressing the polypeptide in a suitable host. Appropriate transcriptional and translational control elements are provided, including a promoter for the DNA sequence, a transcriptional termination site, and translation start and stop codons. The DNA sequence is provided in the correct frame such as to enable expression of the polypeptide to occur in a host compatible with the vector.

The expression vector typically comprises an origin of replication and, if desired, a selectable marker gene such as antibiotic resistance. The expression vector may be a plasmid, a virus, particularly a baculovirus, and the like. Once the nucleotide sequences encoding the antithrombin proteins of the invention have been isolated, they can be manipulated and used to express the protein in a variety of hosts including other organisms, including microorganisms.

Once the nucleotide sequence is identified and known, those skilled in the art can produce large quantities of the protein for therapeutic use. Accordingly, recombinant protein and methods for producing the recombinant protein are encompassed by the present invention. In this manner, the nucleotide sequence encoding the antithrombin protein can be utilized in vectors for expression in various types of host cells, including both procaryotes and eucaryotes, to produce large quantities of the protein, or active analogues, or fragments thereof, and other constructs having antithrombin activity.

Generally, methods for the expression of recombinant DNA are known in the art. See, for example, Sambrook et al., *Molecular Cloning*, Cold Spring Harbor Laboratory (1989). Additionally, host cells and expression vectors, such as the baculovirus expression vector may be employed in carrying out the present invention, as described in U.S. Pat. Nos. 4,745,051 and 4,879,236. In general, a baculovirus expression vector comprises a baculovirus genome containing the gene to be expressed inserted into the polyhedron gene at a position ranging from the polyhedron transcriptional start signal to the ATG start site and under the transcriptional control of a baculovirus polyhedron promoter.

A broad variety of suitable procaryotic and microbial vectors are available. Likewise, the promoters and other regulatory agents used in expression of foreign proteins are available in the art. Promoters commonly used in recombinant microbial expression vectors are known in the art and include the beta-lictamase (penicillinase) and lactose promoter systems (Chang et al. (1978) *Nature*, 275:615 and Goeddel et al. (1979) *Nature*, 281:544); A tryptophan (TRP) promoter system (Goeddel et al. (1980) *Nucleic Acids Res.*, 8:4057 and the EPO Application Publication No. 36,776); and the Tac promoter (DeBoer et al. (1983) *Proc. Natl. Acad. Sci. USA*, 80:21). While these are commonly used, other microbial promoters are available. Details concerning nucleotide sequences of many have been published, enabling a skilled worker to operably ligate them to DNA encoding the protein in plasmid or viral vectors. See, for example, Siedenlist et al. (1980) *Cell*, 20:269.

Eukaryotic microbes such as yeast may be transformed with suitable protein-encoding vectors. See, e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the desired protein, sequences for polyadenylation and transcription termination, and a selection gene. An exemplary plasmid is YRp7, (Stinchcomb et al. (1979) *Nature*, 282:9; Kingsman et al. (1979) *Gene*, 7:141; Tschemper et al. (1980) *Gene*, 10:157). This plasmid contains the trp1 gene, which provides a selection marker for a mutant strain of yeast lacking the ability to grow in tryptophan, for example ATCC No. 44076 or PEP4-1 (Jones, *Genetics* 85, 12 (1977)). The presence of the trp1 lesion in the yeast host cell genome then provides an effective environment for detecting transformation by growth in the absence of tryptophan. Suitable promoting sequences in yeast vectors include the promoters for metallothionein, alcohol dehydrogenase, adenylate cyclase, 3-phosphoglycerate kinase (Hitzeman et al. (1980) *J. Biol. Chem.* 255:2073) and other glycolytic enzymes (Hess et al. (1968) *J. Adv. Enzyme Reg.*, 7:149; and Holland et al. (1978) *Biochemistry*, 17:4900) such as enolase, glyceraldehydes-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al. EPO Publication. No. 73,657.

The compositions of the present invention can be formulated into pharmaceutical preparations for therapeutic use. As antithrombin agents, the compositions find use in the treatment of venous thrombosis, vascular shunt occlusion and thrombin-included disseminated intravascular coagulation.

The compositions of the invention can be used alone or in combination with other antithrombin and therapeutic agents. Other agents are known in the art.

The antithrombin compositions can be formulated according to known methods to prepare pharmaceutically useful compositions, such as by admixture with a pharmaceutically acceptable carrier vehicle. Suitable vehicles and their formulation are described, for example, in *Remington's Pharmaceutical Sciences* 19th ed., Osol, A. (ed.), Mack Easton PA (1980). In order to form a pharmaceutically acceptable composition suitable for effective administration, such compositions will contain an effective amount of the antithrombin protein, either alone, or with a suitable amount of carrier vehicle.

Additional pharmaceutical methods may be employed to control the duration of action. Controlled release preparations may be achieved by the use of polymers to complex or absorb the compositions. The controlled delivery may be exercised by selecting appropriate macromolecules (for example, polyesters, polyamino acids, polyvinyl pyrrolidone, ethylene-vinylacetate, methylcellulose, carbosymethylcellulose, or protamine sulfate). The rate of drug release may also be controlled by altering the concentration of such macromolecules.

Another possible method for controlling the duration of action comprises incorporating the therapeutic agents into particles of a polymeric substance such as polyesters, polyamino acids, hydrogels, poly(lactic acid) or ethylene vinylacetate copolymers. Alternatively, it is possible to entrap the therapeutic agents in microcapsules prepared, for example, by coacervation techniques or by interfacial polymerization, for example, by the use of hydroxymethyl cellulose or gelatin-microcapsules or poly (methylmethacrylate) microcapsules, respectively, or in a colloid drug delivery system, for example, liposomes, albumin, microspheres, microemulsions, nanoparticles, nanocapsules, or in macroemulsions. Such teachings are disclosed in *Remington's Pharmaceutical Sciences* (1980).

In more specific embodiments, a polypeptide of the invention may be converted into a pharmaceutically acceptable salt. It may be converted into an acid additional salt with an organic or inorganic acid. Suitable acids include acetic, succinic and hydrochloric acid. Alternatively, the peptide may be converted into a carboxylic acid salt such as the ammonium salt or an alkali metal salt such as the sodium or potassium salt.

A polypeptide or pharmaceutically acceptable salt thereof may be used in a pharmaceutical composition, together with a pharmaceutically acceptable carrier or excipient therefor. Such a formulation is typically for intravenous administration (in which case the carrier is generally sterile saline or water of acceptable purity). A polypeptide can therefore be used for the therapy and prophylaxis of thromboses and thromboembolisms in a human or other mammal, including the prophylaxis of post-operative thromboses, for acute shock therapy (for example for septic or polytraumatic shock), for the therapy of consumption coagulopathics, in hemodialyses, haemoseparations and in extracorporeal blood circulation. In one embodiment of the invention, the polypeptide or salt thereof can be coadministered with a plasminogen activator, such as tissue plasminogen activator.

The dosage depends especially on the specific form of administration and on the purpose of the therapy or prophylaxis. The size of the individual doses and the administration regime can best be determined by way of an individual judgment of the particular case of illness; the methods of determining relevant blood factors required for this purpose are familiar to the person skilled in the art. Normally, in the case of an injection the therapeutically effective amount of the compounds according to the invention is in a dosage range of from approximately from 0.005 or 0.01 to approximately 0.05 or 0.1 mg/kg body weight, preferably from approximately 0.01 to approximately 0.05 mg/kg body weight.

The administration is effected by intravenous, intramuscular or subcutaneous injection. Accordingly, pharmaceutical compositions for parenteral administration in single dose form contain per dose, depending on the mode of administration, from approximately 0.4 to approximately 7.5 mg of the compound according to the invention. In addition to the active ingredient these pharmaceutical compositions usually also contain a buffer, for example a phosphate buffer, which is intended to keep the pH value between approximately 3.5 and 7, and also sodium chloride, mannitol or sorbitol for adjusting the isotonicity. The preparations may be freeze-dried or dissolved. An antibacterially active preservative may be included, for example from 0.2 to 0.3% 4-hydroxybenzoic acid methyl ester or ethyl ester.

A composition for topical application can be in the form of an aqueous solution, lotion or gel, an oily solution or suspension or a fat-containing or, especially, emulsified ointment. A composition in the form of an aqueous solution is obtained, for example, by dissolving the active ingredients according to the invention, or a therapeutically acceptable salt thereof, in an aqueous buffer solution of from e.g., pH 4 to pH 6.5 and, if desired, adding a further active ingredient, for example an anti-inflammatory agent, and/or a polymeric binder, for example polyvinylpyrrolidone, and/or a preservative. The concentration of active ingredients is from approximately 0.1 to approximately 1.5 mg, preferably from 0.25 to 1.0 mg, in 10 ml of a solution or 10 g of a gel.

An oily form of administration for topical application is obtained, for example, by suspending the active ingredient according to the invention, or a therapeutically acceptable salt thereof, in an oil, optionally with the addition of swelling agents, such as aluminum stearate, and/or surfactants (tensides) having an HLB value ("hydrophilic-lipophilic balance") of below 10, such as fatty acid monomers of polyhydric alcohols, for example glycerin monostearate, sorbitan monolaurate, sorbitan monostearate or sorbitan monooleate. A fat-containing ointment is obtained, for example, by suspending the active ingredient according to the invention, or a salt thereof, in a spreadable fatty base, optionally with the addition of a tenside having an HLB value of below 10. An emulsified ointment is obtained by triturating an aqueous solution of the active ingredient according to the invention, or a salt thereof, in a soft, spreadable fatty base with the addition of a tenside having an HLB value of below 10. All these forms for topical application can also contain preservatives. The concentration of active ingredient is from approximately 0.1 to approximately 1.5 mg, preferably from 0.25 to 1.0 mg, in approximately 10 g of base.

In addition to the compositions described above and pharmaceutical compositions analogous thereto that are intended for direct medicinal use in the body of a human or a mammal, the present invention relates also to pharmaceutical compositions and preparations for medicinal use outside the living body of humans or mammals. Such compositions and preparations are used especially as anticoagulant additives to blood that is being subjected to circulation or treatment outside the body (for example haemoseparation). Such preparations, such as stock solutions or alternatively preparations in single dose form, are similar in composition to the injection preparations described above; however, the amount of concentration of active ingredient is advantageously based on the volume of blood to be treated or, more precisely, on its thrombin content. Depending on the specific purpose, the suitable dose is from approximately 0.01 to approximately 1.0 mg of the active ingredient/liter of blood, although the upper limit may still be exceeded without risk as the agent is harmless even in relatively high amounts.

The following examples are offered by way of illustration and not by way of limitation.

EXPERIMENTAL

Collection of Salivary Glands

*Simulium vittatum* females were taken from a continuous laboratory culture maintained at the University of Arizona (Bernardo et al., (1986), *Ann. Ent. Soc. Am* 79:610–621). Salivary glands were removed surgically from females maintained on water ad libitum for 48 hours to enhance optimum protein secretion prior to dissection. (Cupp et al. (1993), *J. Insect Physiol.* 39:817–821). Glands were removed on a clean glass slide in chilled 0.15 M NaCl (saline) and transferred to an Eppendorf tube containing 50 $\mu$l of chilled saline on ice. Up to 250 glands were accumulated per vial and stored at −70° C. until needed.

Physical Characterization of *S. vittatum* Anti-Thrombin

Crude salivary gland lysate was used to determine heat stability (56° C. for 1 hour), alcohol precipitation (90% ethanol), trypsinization for 30 min and stability to 60% acetonitrile and 0.1% trifluoracetic acid (TFA) (1 h). Thrombin inhibition assays were conducted as described by Abebe et al. (1994), *J. Med. Ent.* 31:908–911.

Anticoagulant Purification

One thousand eight hundred and fifty glands were lysed by four cycles of rapid freeze-thawing (between liquid $N_2$ and 37° C.). The lysate was spun at 10,000 g for 15 min at 4° C. and the supernatant fluid was removed directly from the Eppendorf tube with the aid of a tuberculin syringe fitted with a plastic automatic pipette tip. One hundred microliters of saline was drawn into the syringe with lysate and gently mixed. The pipette tip was replaced with a 0.2 $\mu$m pore size Acrodisc 13 filter (Gelman Sciences, Ann Arbor, Mich.) and the salivary suspension was directly applied to a 10 kDa molecular weight cut-off Centricon filter (Amicon. Beverly, Mass.). Two hundred microliters of saline were passed through the filter membrane twice and added to the salivary proteins which were concentrated by centrifugation using a JA-20 rotor at 4100 rpm in a Beckman JA 20–21 induction drive centrifuge (Beckman, Fullteron, Calif.) for 1.5 hours at 4° C. The retentate contained most of the activity and was used as starting material for purification of the anticoagulant components using an LDC Analytical (thermo Separation Products, Fremont, Calif.) high performance liquid chromatography (HPLC) system.

The anticoagulant was isolated by a two-step purification procedure using a reversed phase C-8 macrosphere column (Alltech, Dearfield, Ill.). In both steps the mobile phases were 15% acetonitrile/water (A) and 50% acetonitrile/water (B), each containing 0.1% TFA. The first purification step followed the protocol of 0–10 min at 100% A, 10–70 min with a gradient of 0–100% B, then 70–80 min at 100% B. The protocol for the second purification step was 0.10 min at 100% A, followed by gradients of 10–24 min=0–39% B, 24–52 min=39–49% B, then 52–70 min at 49% B. Fractions of 1 ml were collected in Eppendorf Tubes with the aid of a Gilson FC-100K fractionator (Gilson, Middleton, Wis.). Ten microliters of a 1% bovine serum albumin (BSA) solution were added to a 50 µl aliquot of each fraction before drying in a Juan RC1010 centrifugal vacuum concentrator (Juna, Los Gatos, Calif.) and stored at −70° C. until needed.

Detection and Isolation of Fractions Anti-Thrombin Activities

Anti-thrombin activities for all fractions were measured as described by Abebe et al. (1994), *J. Med. Ent.* 31:908–911, except that thrombin was reduced to 3.5 ng. To rule out possible cross activity against factor Xa and to determine where the fraction with anti-factor Xa activity eluted in relation to the anti-thrombin, the enzyme inhibition assay for Xa was conducted using the procedure described above with the same modification. Tests were done in duplicate for each fraction. For further purification, the fraction with anti-thrombin activity was rechromatographed under the same conditions with a modified gradient. Anti-thrombin activity was tested for each of the fractions as outlined above. Inhibition was expressed as a percentage of the control which contained only BSA. Anticoagulant activity of the anti-thrombin fraction was determined with the recalcification time test.

Determination of Molecular Weight, Amino Acid Composition and N-Terminal Sequencing The determination of the molecular weight by matrix assisted laser desorption mass spectrometry (MALD-MS) (Hillenkamp et al. (1991), *Analyt. Chem.* 63:1193–1202) and amino acid composition and N-terminal sequencing was made at the Harvard Microchemistry Facilities (Cambridge, Mass.). Version 7 of the GCG program (Genetics Computer Group, Inc., Madison, Wis.) was used to search for N-terminal sequence homology.

PCR Production of cDNA for Coding Region

Knowledge of the N-terminal protein amino-acid sequence was used to construct degenerate, forward primers which were used along with a polymerase chain reaction (PCR) technique known as 3' RACE (random amplification of cDNA ends), to amplify specific target DNA. The DNA pool was generated by reverse-transcription of *S. vittatum* salivary gland mRNA. The oligo-dT template (16T) used to generate the DNA pool had 13 extra bases attached to the 5' end which resulted in a known "tag" being added to each cDNA. A PCR that included the tagged cDNA, the anti-thrombin specific degenerate primers and the tagged oligo-dT primer generated a product of approximately 700 base pairs. See, SEQ ID NO:1.

The PCR product was gel purified, quantified and cloned using commercially-available Invitrogen TA Cloning Vector. The cDNA was sequenced by methods available in the art and the sequence is provided in SEQ ID NO: 1.

Translation of the cDNA code produced the putative amino acid sequence for the mature protein. The calculated molecular weight of the putative protein (11,302 Daltons) is slightly less than the molecular weight of the pure, active protein isolated from *S. vittatum* SGE and determined by mass spectroscopy (11,334+28 Daltons). This may indicate that some post-translational modification to simulidin occurs during protein translation.

The presence of more than 200 bases beyond the stop codon at the 3' end of the DNA suggests that the message for this protein is highly regulated by *S. vittatum* salivary gland cells in vivo. Analysis of the putative amino acid structure indicates that the mature protein contains 3 disulfide bonds which may be important to function. In addition, the C-terminus is highly acidic, which is a feature similar to the well-studied anti-thrombin protein, hirudin.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

Many modifications and other embodiments of the invention will come to mind in one skilled in the art to which this invention pertains having the benefit of the teachings presented in the foregoing descriptions and the associated drawings. Therefore, it is to be understood that the invention is not to be limited to the specific embodiments disclosed. Although specific terms are employed, they are used in a generic and descriptive sense only and not for purposes of limitation, and that modifications and embodiments are intended to be included within the scope of the appended claims.

That which is claimed:

1. A method for inhibiting clotting in blood, said method comprising combining an affective amount of an anti-thrombin protein with a volume of blood, wherein said protein comprises the amino acid sequence set forth in SEQ ID NO:2.

2. A method for inhibiting clotting in blood, said method comprising the steps of:
    culturing a host cell comprising an isolated nucleic acid molecule which encodes an anti-thrombin protein having an amino acid sequence at least 80% identical to the amino acid sequence of SEQ ID NO:2 under conditions suitable to express said protein; and
    combining an effective amount of said protein isolated from said host cell or host cell culture supernatant with a volume of blood.

3. The method of claim 2, wherein said polypeptide has an amino acid sequence at least 90% identical to the amino acid sequence of SEQ ID NO:2.

4. The method of claim 2, wherein said polypeptide has an amino acid sequence at least 95% identical to the amino acid sequence of SEQ ID NO:2.

* * * * *

UNITED STATES PATENT AND TRADEMARK OFFICE
CERTIFICATE OF CORRECTION

PATENT NO. : 6,825,168 B2
DATED : November 30, 2004
INVENTOR(S) : Cupp et al.

It is certified that error appears in the above-identified patent and that said Letters Patent is hereby corrected as shown below:

Column 13,
Line 3, "affective" should read -- effective --.

Signed and Sealed this

Fifth Day of April, 2005

JON W. DUDAS
*Director of the United States Patent and Trademark Office*

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 532 base pairs
      (B) TYPE: nucleic acid
      (C) STRANDEDNESS: single -continued (D) TOPOLOGY: linear (ii) MOLECULE TYPE: cDNA (vi) ORIGINAL SOURCE:
         (A) ORGANISM: Simulium vittatum (ix) FEATURE:
         (A) NAME/KEY: CDS
         (B) LOCATION: 1..294

(xi) SEQUENCE DESCRIPTION: SEQ ID NO: 1:

```
GAG GTG GCG AAT TTG CAG GAC CAT CGA GCT GTT GAA TTT GTG TGC GAG      48
Glu Val Ala Asn Leu Gln Asp His Arg Ala Val Glu Phe Val Cys Glu
 1               5                  10                  15

AAG GAT ACT GAA AAC CAG CAT GGT TCC GAT TGC CTG CTT TCT TGT GAC      96
Lys Asp Thr Glu Asn Gln His Gly Ser Asp Cys Leu Leu Ser Cys Asp
            20                  25                  30

GTG ATG TTC TGG GAT ACC AAA AAC GAG AAC AAC AAG GAA TAT GAA GAC     144
Val Met Phe Trp Asp Thr Lys Asn Glu Asn Asn Lys Glu Tyr Glu Asp
        35                  40                  45

AGA TAC AAT TTG TGC AAA CAT TCA GCC GCT TCC GAA GAG AAC ATT TGT     192
Arg Tyr Asn Leu Cys Lys His Ser Ala Ala Ser Glu Glu Asn Ile Cys
 50                  55                  60

GAT CGC AAT GAA GAA TTG AGA GCC TGT TTC TTG CAT GAT TCG TCA TAC     240
Asp Arg Asn Glu Glu Leu Arg Ala Cys Phe Leu His Asp Ser Ser Tyr
65                  70                  75                  80

GAA GAG ACT TCG GAC GAA TAT GAA ATA ACC TAC AGC ATG GAT TCC CTG     288
Glu Glu Thr Ser Asp Glu Tyr Glu Ile Thr Tyr Ser Met Asp Ser Leu
                85                  90                  95

TGA TGA TCAAACATTG GTAATAGTTC AATTGATCGA AATATGCAGA AACCGTCCAC     344
 *   *
GGTAGTGTAA TTATAACCCA TGTTGTTCGC ATTGTACTCT AATTCTACTC CGTTCATATA     404

TGGCTGATGA GTGCCATCCA GCCAATGTGA ACAGGAGTA TAAAAAGCAC AATGTGGGTG      464

ACAGTCCCAT TCACACAATA TGCAAATAAA ATAATGGAAA TGACCCCAAA AAAAAAAAAA     524

AAAAAAA                                                              532
```

(2) INFORMATION FOR SEQ ID NO: 2:

(i) SEQUENCE CHARACTERISTICS:
        (A) LENGTH: 96 amino acids
        (B) TYPE: amino acid
        (D) TOPOLOGY: linear (ii) MOLECULE TYPE: protein (xi) SEQUENCE DESCRIPTION: SEQ ID NO: 2:

```
Glu Val Ala Asn Leu Gln Asp His Arg Ala Val Glu Phe Val Cys Glu
 1               5                  10                  15

Lys Asp Thr Glu Asn Gln His Gly Ser Asp Cys Leu Leu Ser Cys Asp
            20                  25                  30

Val Met Phe Trp Asp Thr Lys Asn Glu Asn Asn Lys Glu Tyr Glu Asp
        35                  40                  45

Arg Tyr Asn Leu Cys Lys His Ser Ala Ala Ser Glu Glu Asn Ile Cys
 50                  55                  60

Asp Arg Asn Glu Glu Leu Arg Ala Cys Phe Leu His Asp Ser Ser Tyr
65                  70                  75                  80

Glu Glu Thr Ser Asp Glu Tyr Glu Ile Thr Tyr Ser Met Asp Ser Leu
                85                  90                  95
```